US006436343B1

(12) United States Patent
Bechini

(10) Patent No.: US 6,436,343 B1
(45) Date of Patent: Aug. 20, 2002

(54) METHOD FOR THE COLD STERILIZATION OF A TUNNEL-TYPE OVEN FOR PHARMACEUTICAL USE, AND OVEN FOR CARRYING OUT SAID METHOD

(75) Inventor: Claudio Bechini, Castelnuovo Berardenga (IT)

(73) Assignee: Libra Pharmaceutical Technologies, Florence (IT)

( * ) Notice: Subject to any disclaimer, the term of this patent is extended or adjusted under 35 U.S.C. 154(b) by 0 days.

(21) Appl. No.: 09/403,556

(22) PCT Filed: Apr. 23, 1998

(86) PCT No.: PCT/IB98/00623

§ 371 (c)(1),
(2), (4) Date: Oct. 25, 1999

(87) PCT Pub. No.: WO98/48854

PCT Pub. Date: Nov. 5, 1998

(30) Foreign Application Priority Data

Apr. 28, 1997 (IT) .......................................... B097A0251

(51) Int. Cl.[7] .............................. A61L 2/00; A61L 9/00
(52) U.S. Cl. .......................... 422/28; 422/33; 422/292; 422/295; 422/304; 422/305; 53/167; 53/425
(58) Field of Search ...................... 53/167, 425, 426, 53/26, 28, 33, 292, 295, 304; 422/305

(56) References Cited

U.S. PATENT DOCUMENTS

| 3,820,300 | A | * | 6/1974 | Reinecke et al. ............. 53/167 |
| 3,942,299 | A | * | 3/1976 | Bory .......................... 53/167 |
| 4,014,158 | A | * | 3/1977 | Rausing ....................... 53/167 |
| 4,375,145 | A | * | 3/1983 | Mosse et al. .................. 53/425 |
| 4,391,080 | A | * | 7/1983 | Brody et al. .................. 53/167 |
| 5,534,222 | A | * | 7/1996 | Kelbrick et al. ............... 422/28 |

FOREIGN PATENT DOCUMENTS

| EP | 0 394 734 A1 | 4/1990 |
| EP | 0 624 518 A3 | 4/1994 |
| FR | 2.084.037 | 12/1971 |
| WO | WO 97/09026 | 3/1997 |
| WO | WO 97/47331 | 12/1997 |

* cited by examiner

*Primary Examiner*—Robert J. Warden, Sr.
*Assistant Examiner*—Imad Soubra
(74) *Attorney, Agent, or Firm*—William J. Sapone; Coleman Sudol Sapone P.C.

(57) ABSTRACT

A method for the cold sterilization of a tunnel-type oven (1) for the hot sterilization of bottles, having an input chamber (3), a hot sterilization chamber (4), a cooling chamber (5) and a conveyor (6). The method consists of a sequence of operating phases which have to be carried out periodically when the oven is empty. The method includes airtightly closing the input (31) and output (51) openings of the oven (1), suppying a pre-defined amount of cold sterilization fluid mixed with air, until all the inner surfaces of the oven (1) are reached by the fluid, opening a recycling duct (37); stopping the supply of cold sterilization fluid, and supplying the oven (1) with humidity and temperature controlled air.

15 Claims, 2 Drawing Sheets

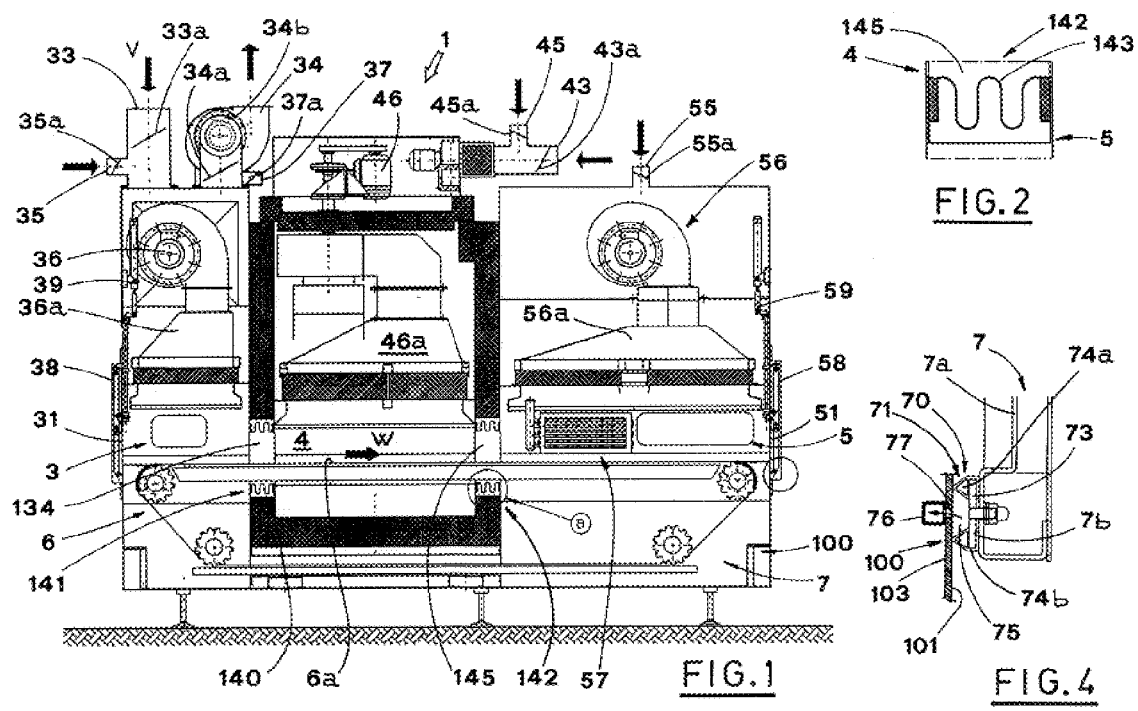

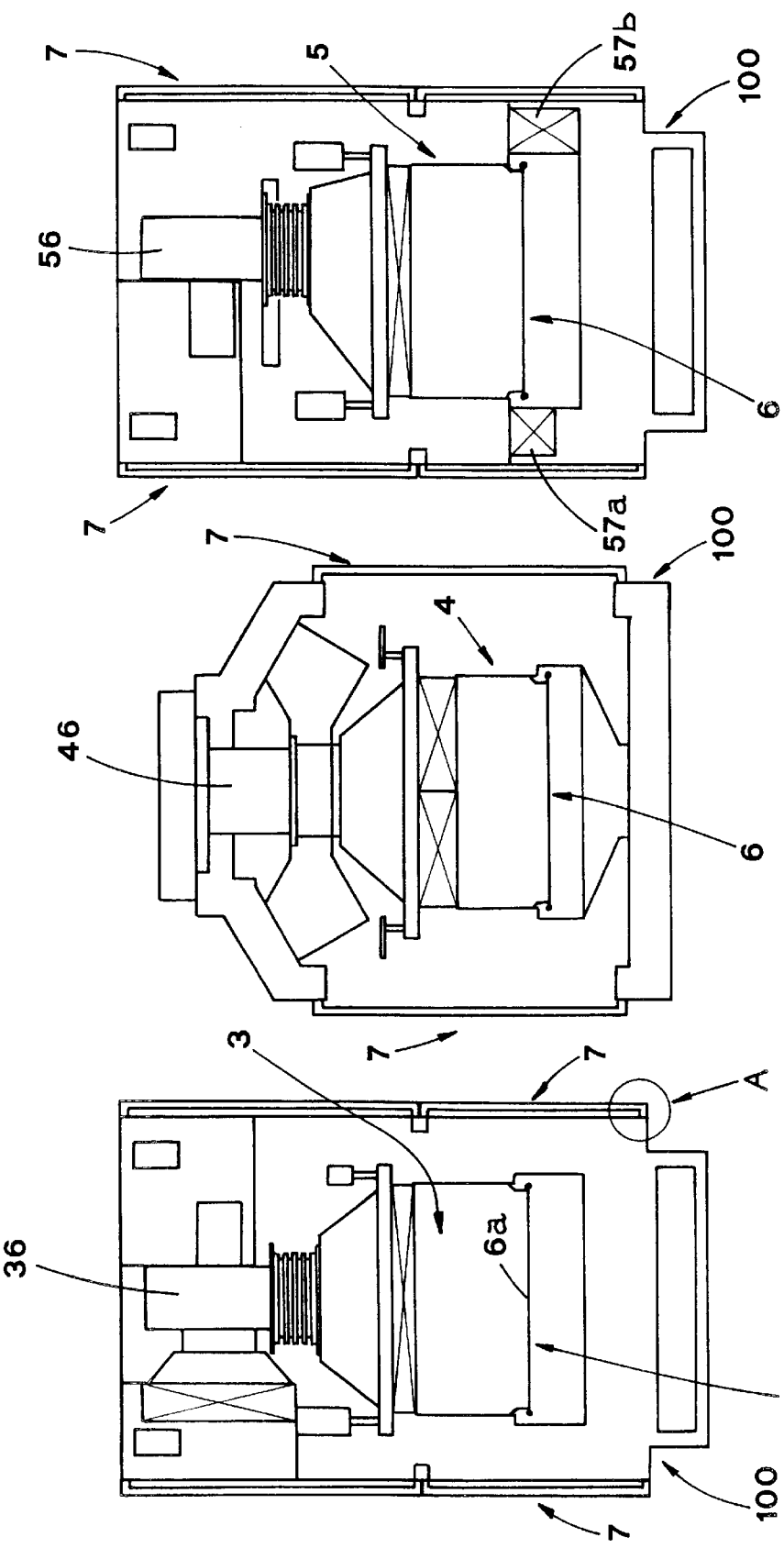

US 6,436,343 B1

METHOD FOR THE COLD STERILIZATION OF A TUNNEL-TYPE OVEN FOR PHARMACEUTICAL USE, AND OVEN FOR CARRYING OUT SAID METHOD

TECHNICAL FIELD

The present invention relates to the technical field concerning the sterilisation of apparatuses or bottles for pharmaceutical use.

More particularly, the present invention relates to a method for sterilising the inside of a bottles sterilisation oven, and to an oven which carries out said method.

BACKGROUND ART

It is known that all the different kinds of bottles for pharmaceutical use, which are made of glass or the like, must be submitted to a sterilisation process before filling them with a drug, in order to destroy or inactivate all the microorganisms that potentially could adulterate the bottles content, or that could be harmful for a patient to which said drug has to be given.

The bottles sterilisation is usually carried out at high temperatures, inside a special sterilisation oven, which is configured as a "tunnel", and which is stepless operated, for productivity purposes.

The known sterilisation tunnel-type ovens normally comprise three cascade-connected and intercommunicating sections: an input chamber, a sterilisation chamber, also called hot chamber, and a cooling chamber for the sterilised bottles. The three above sections are crossed by a tape conveyor, that forwards the aforesaid bottles in sequence through all the sections.

The input chamber has an input door, through which the bottles, coming from a washing station, are fed to the oven. At the opposite end, the cooling chamber is provided with an output door for communicating with a sterile room, wherein bottles are filled with a drug and then sealed.

The hot chamber is provided with suitable heaters, operable to heat the said chamber to a given temperature, which is high enough to sterilise all the bottles continuously passing therein.

Bottles stay in the cooling chamber until their temperature attains a value approaching that of the subsequent sterile room. Said chamber is suitably provided with working fluid type heat exchangers, which help in lowering the air temperature inside the chamber, and consequently in lowering the bottles temperature.

All the sterilisation oven sections are normally submitted to a laminar flow of air filtered by H.E.P.A. filters of suitable retention characteristic features. They are kept in a slight plenum condition, in order to avoid any non-filtered air, which is therefore contaminated by particles and microorganisms, to flow into the oven.

But, in the conventional sterilisation ovens, neither the input chamber nor the cooling chamber are intrinsically sterile. In fact, although they are subject to a continuous laminar flow of filtered air, their inner surfaces could contain some contaminating agent, that could pollute the bottles. This is a serious drawback, particularly for the cooling chamber, which contains already sterilised bottles of course, the hot chamber is intrinsically sterile.

The aforesaid possibility of bottles contamination, although it is normally very poor, is taken in particular account by all the pharmaceutical companies and surveillance organisations, and a great number of requests for ovens provided with a sterile cooling chamber is arising.

Some ovens provided with periodical sterilisation procedures for the cooling chamber are known, particularly by heating it to a temperature similar to those reached in the hot chamber, in order to kill all the pathogenic agents. This solution is extremely expensive and difficult to carry out and to sell. In fact, because of the cooling chamber size, high power heating assemblies must be provided; all the power lines and apparatuses that carry the power to the oven must be sized accordingly, and then practically doubled with respect to a conventional sterilisation oven.

DISCLOSURE OF THE INVENTION

It is an object of the present invention to propose a method for the periodical sterilisation of the cooling chamber, and of the whole sterilisation oven, which can be carried out without heating the same oven.

A further object of the present invention is to propose a such method which doesn't significantly improve the oven production costs nor its power consumption.

A further object is to propose a sterilisation oven which is totally cold sterilisable, accordingly to the aforesaid method.

The aforesaid objects are achieved by a method comprising the steps of:

air tightly closing oven input and output openings and input and output ducts;

opening forced input means, for introducing a mixture of air and of sterilisation fluid into the oven;

supplying a pre-defined amount of a mixture of sterilisation fluid and air, until a pre-defined static pressure is attained;

opening at least one output duct for the sterilisation fluid;

stopping the supply of the sterilisation fluid, and supplying the oven with humidity controlled air, until the percentage of said sterilisation fluid inside the oven falls down to a pre-defined value;

closing said forced input means and said output duct, and re-opening the input and output opening.

BRIEF DESCRIPTION OF THE DRAWINGS

The characteristic features of the invention are set out in the following, with particular reference to the accompanying drawings, in which:

FIG. 1 shows a schematic sectional view of a sterilisation tunnel-type oven, made according to the present invention;

FIG. 2 shows an enlarged view of the detail B of FIG. 1;

FIG. 3 shows a schematic front sectional view of the oven of FIG. 1, at the input chamber;

FIG. 4 shows an enlarged sectional view of the detail A of FIG. 3;

FIG. 5 shows a schematic front sectional view of the oven of FIG. 1, at the hot chamber;

FIG. 6 shows a schematic front sectional view of the oven of FIG. 1, at the cooling chamber.

BEST MODE OF CARRYING OUT THE INVENTION

Referring now to FIG. 1, numeral 1 indicates a sterilisation, tunnel-type oven, for the continuous hot sterilisation of bottles for pharmaceutical products. Said oven 1 substantially comprises a supporting frame 100, of approximately parallelepipedal shape. Inside the frame 100 an input chamber 3, a hot sterilisation chamber 4 and a cooling chamber 5 are successively arranged. These three chambers communicate one each other, by means of a first passage 134, between the input chamber 3 and the sterilisation chamber 4, and a second passage 145, between this latter and the cooling chamber 5. The input chamber 3 and cooling chamber 5 are also respectively provided with an input opening 31 and with an output opening 51, aligned with the passages 134,145. The input opening 31 receives the bottles coming from a previous washing apparatus, while the output opening 51 is connected in a know way to a sterile room, or to an insulating environment, wherein the sterilised bottles are filled with the corresponding pharmaceutical product, and then sealed.

Chambers 3,4,5 are moreover crossed by a continuous tape conveyor 6, which is driven to a direction W at a given speed, generally variable according to known sequences. The tape conveyor 6 carries the above cited bottles on its upper branch 6a, during the normal oven operating procedures, from the input opening 31 to the output opening 51.

The operating modes of the oven 1, fit to obtain a complete hot sterilisation of bottles, are known, and they will not be detailed in the following. They are totally automated and handled by an electronic control unit, not shown in the drawings.

The input chamber 3 has a first ventilation assembly 36, provided with a flow conveyor 36a and with a corresponding H.E.P.A. filter, and fit to generate a laminar flow of sterile air in the said chamber 3, according to known techniques (see also FIG. 3). The first ventilation assembly 36 is connected to the external environment by means of a first input duct 33, provided with a flow regulating valve 33a. An air output duct 34 is also provided at the upper end of the input chamber 3, and has an output flow regulating valve 34a and a discharge fan 34b. Said valve 34a and fan 34b are operated in a phase relationship with the first ventilation assembly 36.

A first forced input duct 35 of a cold sterilisation fluid joins the first input duct 33 just downstream of the flow regulating valve 33a with respect to the air input flow, which is indicated with the V arrow in FIG. 1. Said duct 35 is provided with a first flow regulating valve 35a, driven according to pre-defined periodic sequences, in order to allow the input chamber to be cold sterilised.

The first forced input duct 35 is connected to a source of that sterilisation fluid, not shown. This latter preferably consists of a suitably measured mixture of hydrogen peroxide and air, whose temperature and humidity is suitably controlled. The mixture is provided by means of a known supply device, a rotating vane centrifugal pump.

At the upper end of the input chamber 3, recycling or evacuating means 37 for the hydrogen peroxide is provided, fit to allow the same to be drained away from the oven 1, or its recycling and re-routing toward the supply device. The recycling or evacuating means consists of a duct, extending from the air output duct 34, just upstream of the flow regulating valve 34a and provided with its own flow regulating valve 37a, operated in a phase relationship with the same valve 34a. The duct 37 is connected to known recycling means for recycling the hydrogen peroxide or, optionally, to known exhausting means, both not shown.

The hot sterilisation chamber 4 is provided in turn with a second ventilation assembly 46, provided with its own flow conveyor 46a and with a corresponding H.E.P.A. filter, and fit to generate a laminar flow of sterile air (see also FIG. 5). The second ventilation assembly 46 is connected to the external environment by means of a second input duct 43, which is also provided with its flow regulating valve 43a.

A second forced input duct 45 of hydrogen peroxide joins the second input duct 43, downstream of the flow regulating valve 43a. Said duct is provided with a second flow regulating valve 45a, operable according to pre-defined periodic sequences, in a phase relationship with the operation of the first flow regulating valve 35a.

A suitably thick layer of insulating material 140 is externally wrapped all around the hot sterilisation chamber 4, for thermally insulating the same, as well as possible, from the input chamber 3, the cooling chamber 5 and the external environment.

At the aforesaid passages 134,145, corresponding first and second control joints 141,142 are sealingly provided (see detail in FIG. 2), fit to define the perimeter of said passages, to keep them airtight and to allow at the same time the sterilisation chamber 4 to expand and to contract according to its thermal variations.

More particularly, each of said control joints, for instance the second control joint 142, consists of a corrugated plate 143 of elastic metal, which is fixed at its ends to the sterilisation chamber 4 and cooling chamber 5 walls by means of a continuous welding.

A third ventilation assembly 56 is arranged in the upper side of the cooling chamber 5, provided with its own flow conveyor 56a with a corresponding H.E.P.A. filter, and fit to generate a laminar flow of sterile air inside the same chamber 5 (see also FIG. 6). The third ventilation assembly 56 provides a closed loop air circulation, since it draws air from the inside of the same cooling chamber 5, in order to improve the air flow.

A third forced input duct 55 of hydrogen peroxide is arranged at the upper end of the cooling chamber 5. This is provided with a third flow regulating valve 55a, which is operated, according to predefined periodic sequences, in a phase relationship with the operation of the first regulating valve 35a and of the second regulating valve 45a, in order to allow the cooling chamber 5 to be cold sterilised.

The third forced input duct 55 is also connected to the aforesaid source of hydrogen peroxide.

The cooling chamber 5 has a pair of heat exchangers 57, respectively a first one 57a and a second one 57b, fit to drain the heat released by the cooling down bottles. They are arranged in the middle portion of the cooling chamber 5, where the laminar flow direction is reversed.

In fact, the whole oven 1 is hermetically sealed. More particularly, all the frame 100 junctions are made with continuous weldings, and the same frame 100 is provided with side panels 7 for covering the input chamber 3, the hot sterilisation chamber 4 and the cooling chamber 5. (FIGS. 3, 5, 6).

Each one of the above panels 7 has, all around the rim 7b of its inner wall 7a (see FIG. 4), a gasket 71 which, when the panel is its operating position, interposes between the inner wall 7a of the same panel 7 and an outer face 101 of the frame 100. The gasket 71 is made of a shaped plate 73, which is fixed to the rim 7b and which extends all around its boundary, and of a pair of airtight curbs 74a, 74b, fixed in turn to the shaped plate 73 and respectively parallel. The plate 73 and the curbs 74a, 74b define, together with the outer face 101 of the frame 100, an airtight compartment 75.

A suction duct 76 is fixed on the inner face 103 of the frame 100, exactly following the path of the airtight compartment 75. The suction duct 76 is connected to known suction means, which periodically bring said duct to a pressure lower than the atmospheric pressure. A plurality of through holes 77 is made in the frame 100, in order to establish a communication between the suction duct 76 and the airtight compartment 75.

The input opening 31 and the output opening 51 are provided with airtight doors 38,58, connected to respective operating means 39,59, which are preferably automatically operated.

According to the method for the cold sterilisation of the present invention, a sterilisation sequence is periodically performed for the oven 1, and particularly for the input chamber 3 and the cooling chamber 5. These sequences are interlaced with the oven 1 normal operation periods. Of course, as previously explained, due to its high operating temperature, the sterilisation chamber 4 is intrinsically sterile.

Each cold sterilisation sequence happens after the oven 1 normal operation has stopped, and the sterilisation chamber 4 has reached a temperature as low as about 40° Centigrade. The following operating phases are then carried out:

the input opening 31 and the output opening 51 are airtightly sealed, by closing their respective doors 38,59, and the flow regulating valves 33a, 43a, 53a of the input ducts 33,43 and output duct 34 are also closed;

the flow regulating valves 35a, 45a, 55a of the forced input ducts 35,45,55 are opened, and a flow of humidity and temperature-controlled air is introduced into the oven 1;

the first, second and third ventilation assemblies 35,45,55 are then activated, for a given period of time;

a pre-defined amount of hydrogen peroxide is supplied to the oven 1, through the aforesaid forced input ducts 35,45,55, until the hydrogen peroxide propagates completely into the cooling chamber 5, the input chamber 4 and the hot sterilisation chamber 4, and until the air pressure inside the oven reaches a given static pressure;

the recycling or evacuating duct 37 is opened, by opening the flow regulating valve 37a;

the supply of hydrogen peroxide is stopped, and humidity and temperature-controlled air is continuously supplied to the oven 1, until the percentage of the hydrogen peroxide falls under a pre-defined value;

the forced input ducts 35,45,55 and the recycling or evacuating duct 37 are closed, and the input opening 31 and output opening 51 are opened, by removing their closing doors 38,58.

Before the said forced input ducts 35,45,55 opening phase is carried out, a further over-pressurized ventilation phase can be provided for the oven 1, which is carried out by opening the flow regulating valves 33a, 43a, 34a of the input ducts 33,43 and output duct 34, and simultaneously activating the ventilation assemblies 36,46,56 and the discharge fan 34b.

Sterilisation sequences like that described above can be performed either with a given frequence, or after the oven 1 has been opened for maintenance purposes.

The method and oven of the present invention give a first advantage in that they allow, not only the cooling chamber 5 to be perfectly sterilised, thus avoiding the sterilised, cooling down bottles, from being contaminated by microorganisms or any other contaminating agent, which would be otherwise present on the inner surfaces of the same cooling chamber 5, but also in that even the input chamber 3 and the hot sterilisation chamber 4, thus the whole oven 1, are perfectly sterilised.

A further given advantage is that, for obtaining said sterilisation, there is no significant improvement in power consumption, and then of maximum required power supply. Moreover, the oven 1 can be operated, during its normal operating life, at an over-pressure regime, not only with respect to the external environment, but also with respect to the sterile room and to the insulating environment. This allows the oven 1 operating settings and maintenance can be made independently from those of the same sterile room.

Moreover, the oven 1 can be advantageously placed even in a non-clean environment, since it is completely insulated from the external environment.

The subject invention has been obviously described, with reference to the attached drawings, for exemplifying and not limitative purposes, and it is therefore evident that it is possible to apply to it all of those modifications or variations suggested by the practice and by its realisation and use, however included in the field defined by the following claims.

What is claimed is:

1. A method for the cold sterilization of a tunnel-type oven for pharmaceutical purpose, provided with at least one input chamber (3), fit to receive a plurality of bottles to be sterilized from oven input opening (31); at least one hot sterilization chamber (4) for said bottles, subsequently arranged with respect to said input chamber (3) and in communication therewith; at least one cooling chamber (5), subsequently placed with respect to said hot sterilization chamber (4) and in communication therewith, fit to receive sterilized, cooling down bottles, and having at least one oven output opening (51); conveying means (6), for conveying said bottles from said input chamber (3), subsequently to said sterilization chamber (4) and said cooling chamber (5), said oven (1) having a plurality of input ducts (33, 43) for introducing external air into said oven (1), and at least one output duct (34) for draining said air to an external environment, said method consisting essentially of the following operating steps which are periodically carried out:

emptying the tunnel-type oven of bottles;

airtightly closing said oven input opening (31) and said at least one oven output opening (51) and said input ducts (33, 43) and said at least one output duct (34) to airtightly seal the tunnel type oven;

opening forced input means (35, 45, 55), for introducing a mixture of air and a cold sterilization fluid at least into said cooling chamber (5);

supplying a predefined amount of said mixture of sterilization fluid and air, until a predefined static pressure is attained within the airtightly sealed oven;

opening at least one output duct (37) for said sterilization fluid;

stopping the supply of said sterilization fluid, and supplying said oven (1) with humidity controlled air, until a percentage of said sterilization fluid inside said oven (1) falls to a predefined value;

closing said forced input means (34, 45, 55) and said at least one output duct (37), and reopening said oven input opening (31) and said at least one oven output opening (51), to allow entry of bottles into the oven.

2. A method according to claim 1, wherein said sterilization fluid is supplied from three forced sterilization fluid forced input ducts, respectively a first forced input duct (35), a second forced input duct (45) and a third forced input duct (55), respectively placed in said input chamber (3), said hot sterilization chamber (4) and said cooling chamber (5).

3. A method according to claim 1, further comprising before said forced input ducts (34, 45, 55) opening phase, subjecting said oven to an over-pressurized ventilation, through said input ducts (33, 43) and said at least one output duct (34).

4. A method according to claim 1, wherein simultaneously to said sterilization fluid input phase, a first ventilation means (36), a second ventilation means (46) and a third ventilation means (56) are operated, respectively in said input chamber (3), said hot sterilization chamber (4) and said cooling chamber (5), for a predefined period of time.

5. A method according to claim 1, wherein the sterilization fluid is hydrogen peroxide.

6. A method according to claim 5, wherein said hydrogen peroxide is supplied in a vapour phase.

7. A tunnel-type oven for pharmaceutical purposes consisting essentially of; at least one input chamber (3), fit to receive a plurality of bottles to be sterilized from an input opening (31); at least one hot sterilization chamber (4) for said bottles, subsequently arranged with respect to said input chamber (3) and in communication therewith; at least one cooling chamber (5), subsequently placed with respect to said hot sterilization chamber (4) and in communication therewith, fit to receive said cooling down, sterilized bottles, and having at least one output opening (51);

conveying means (6), for conveying said bottles from said input chamber (3), subsequently to said sterilization chamber (4) and said cooling chamber (5);

first ventilation means for ventilating said input chamber (36), second ventilation means for ventilating said hot sterilization chamber (46) and third ventilation for ventilating said cooling chamber (5);

a plurality of external air input ducts (33, 43) and at least one output duct (34) for draining said air to an external environment;

a plurality of doors (38, 58) for airtight closing said input opening (31) and said output opening to airtightly seal the oven for pressurization during sterilization of said oven when empty (51);

a plurality of airtight closing means (70) being panels (7) for covering said input chamber (3), said hot sterilization chamber (4) and said cooling chamber (5);

cold sterilization fluid forced input means (35, 45, 55) for supplying a cold sterilization fluid into said oven (1);

cold sterilization fluid recycling or evacuating means (37) for draining said cold sterilization fluid from said oven (1), until a percentage of said cold sterilization fluid inside the oven (1) falls to a predefined value;

a first control joint (141) and a second control joint (142), respectively arranged at a first entry passage (134) and a second exit passage (145), for airtightly defining a perimeter of said hot sterilization chamber, said first and second control joints allowing the hot sterilization chamber (4) to expand and to contract according to thermal variations independently of the input chamber and cooling chamber.

8. Oven according to claim 7, wherein said forced input means consists of a first duct (35), a second duct (45) and a third duct (55), each respectively having a flow regulating valve (35a, 45a, 55a), and each duct connected to a sterilization fluid supplying source.

9. Oven according to claim 8, wherein said first duct (35), second duct (45) and third duct (55) are respectively arranged in said input chamber (3), hot sterilization chamber (4) and cooling chamber (5).

10. Oven according to claim 7, wherein said recycling or evacuating means (37) consists of at least one recycling or evacuating duct having an output flow regulating valve (37a).

11. Oven according to claim 10, wherein said recycling or evacuating duct (37) is arranged in said input chamber.

12. Oven according to claim 10, wherein said airtight closing means (70) comprises, for each said panel (7): at least one gasket (71), interposed between an outer face (101) of a frame (100) of said oven (1) and an inner face (7a) of said panel (7), near a circumpherntial rim (7b) of the panel, said gasket (71) forming at least one airtight compartment (75) for insulating said oven (1) from an external environment; at least one suction duct (76), fixed to the inner face (103) of said frame (100), exactly following the path of said airtight compartment (75), a plurality of through holes (77) being provided in said frame (100), for establishing a communication between said suction duct (76) and said airtight compartment (75).

13. Oven according to claim 12, wherein said gasket (71) consists of at least one shaped plate (73), fixed to said rim (7b) and at least one pair of parallel airtight curbs (74a, 74b), fixed to said shaped plate (73).

14. Oven according to claim 7, wherein that said airtight closing doors (38, 58) have automatically operated operating means (39, 59).

15. Oven according to claim 7, wherein each said control joint (141, 142) consists of a corrugated plate (143) made of elastic metal, fixed at a first end to said sterilization chamber (4) and at a second end to said input chamber (3) and to said cooling chamber (5), respectively.

* * * * *